United States Patent [19]

Izaguirre-Martinez et al.

[11] Patent Number: 5,645,716
[45] Date of Patent: Jul. 8, 1997

[54] ELECTROPURIFIER AND SOFTENER SYSTEM OF CONTINUOUS FLOW FOR WATER AND LIQUIDS FOR HUMAN, AGRICULTURAL AND INDUSTRIAL CONSUMPTION

[76] Inventors: Jose Antonio Izaguirre-Martinez, Manzanillo #410 Int. 9 Col. Granjas San Isidro 27100, Torreon, Coah.; Juan Pablo Izaguirre-Franco, Zacatecas #104 Col. Las Rosas, 35090, Gomez Palacio, Durango, both of Mexico

[21] Appl. No.: 572,111

[22] Filed: Dec. 14, 1995

[51] Int. Cl.⁶ .................................................. C02F 1/48
[52] U.S. Cl. ............................................. 210/97; 210/243
[58] Field of Search .................................. 210/243, 748, 210/97; 422/22; 204/660, 661

[56] References Cited

U.S. PATENT DOCUMENTS

| | | | |
|---|---|---|---|
| 3,753,886 | 8/1973 | Myers | 210/748 |
| 3,965,008 | 6/1976 | Dawson | 210/243 |
| 5,007,994 | 4/1991 | Snee | 210/243 |

*Primary Examiner*—Matthew O. Savage
*Attorney, Agent, or Firm*—Laurence R. Brown

[57] ABSTRACT

This invention is directed to apparatus for purification of water and liquids for human, agricultural and industrial consumption. A non-ferromagnetic metal body houses graphitized electrodes and a magnetic switching mechanism activated by fluid flowing through the system to change valences of mineral in the fluid and eliminate bacteria, thus purifying and softening the liquid.

5 Claims, 4 Drawing Sheets

ELECTROPURIFIER AND SOFTENER SYSTEM OF CONTINUOUS FLOW FOR WATER AND LIQUIDS FOR HUMAN, AGRICULTURAL AND INDUSTRIAL CONSUMPTION

BACKGROUND OF THE INVENTION

For many years men have tried to improve elements provided by nature to make them more useful for their own benefit. One such element is water. For water treatment, since time immemorial, mankind has used different kinds of filters and methods of purification that go from the simplest to the most sophisticated ones.

The object of the invention is to provide an electropurifying and softening system, of continuous flow, for water and liquids for human, agricultural and industrial consumption, that functions providing all those advantages for purifying and softening the volume of liquids required at the necessary time.

It is well known that at domestic level, apparatus like the one invented are actually totally unknown.

It is the intention of the art offered, to give solution to a problem, daily present in many places, for which nobody has found a solution to date.

DESCRIPTION OF THE INVENTION

Figure 1:
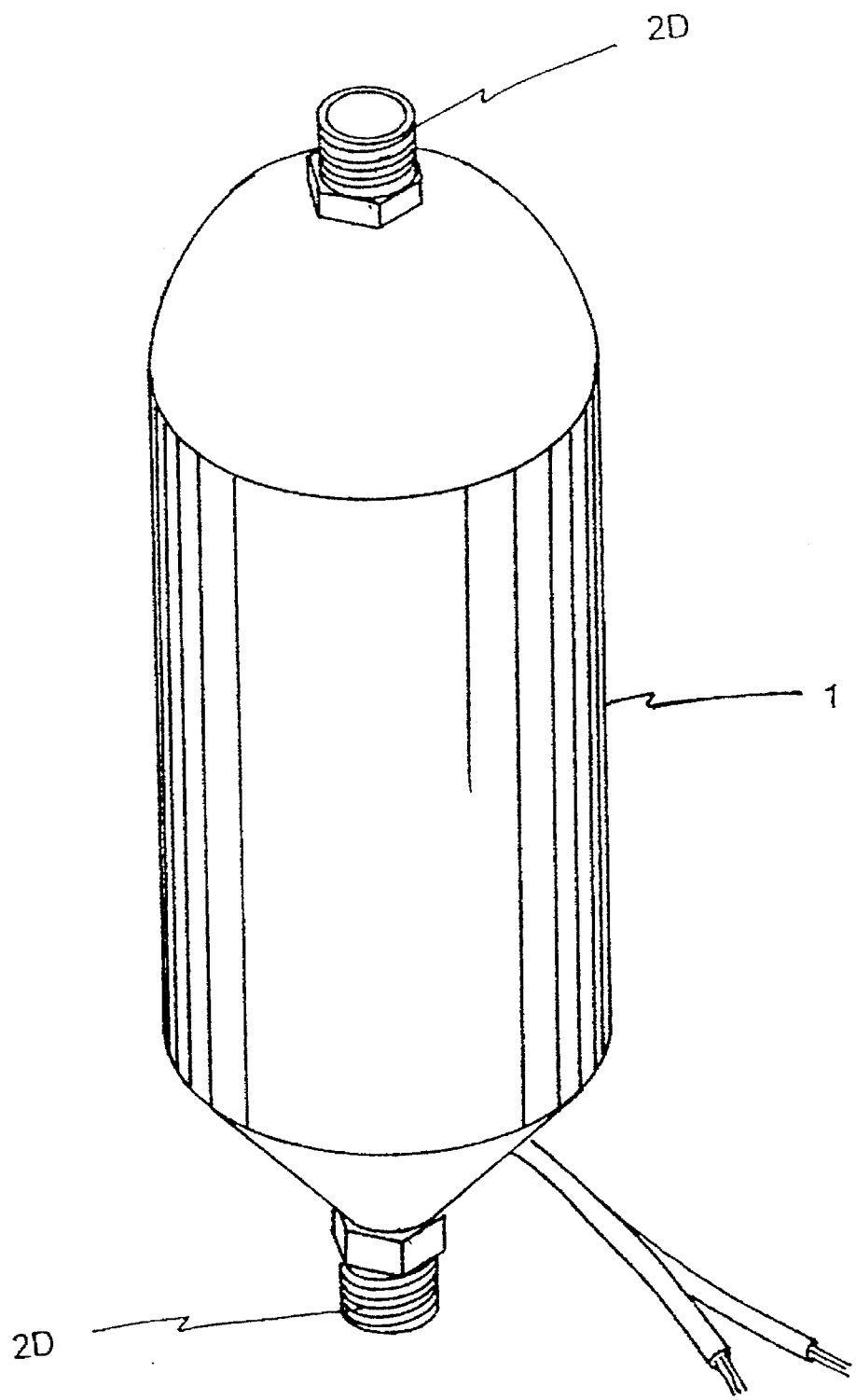
FIG. 1 shows an isometric view of the electropurifying and softening system, of continuous flow, for water and liquids for human, agricultural and industrial consumption.
Figure 2:
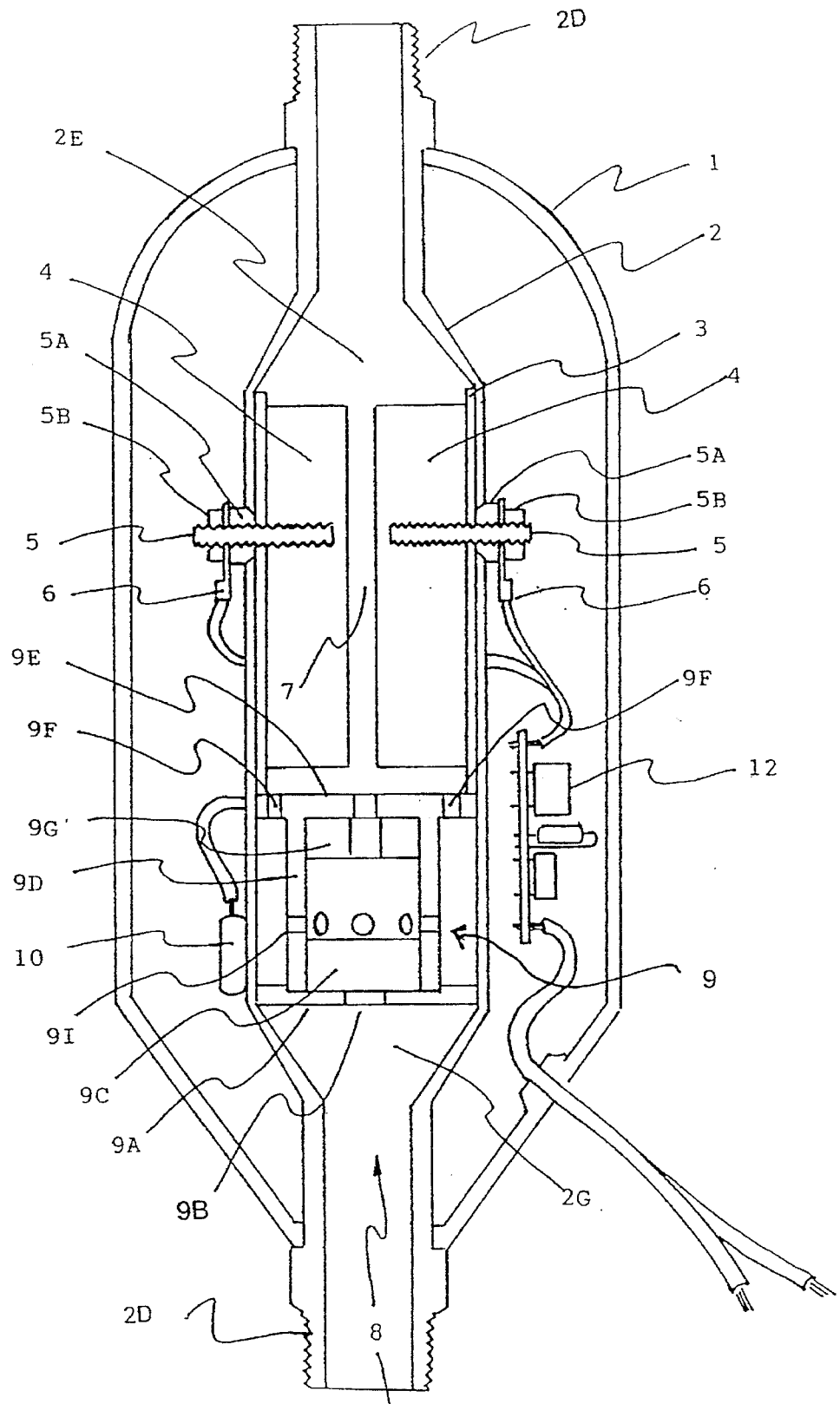
FIG. 2 shows a longitudinal sectional view of the electropurifying and softening system, of continuous flow, for water and liquids for human, agricultural and industrial consumption.
Figure 3:
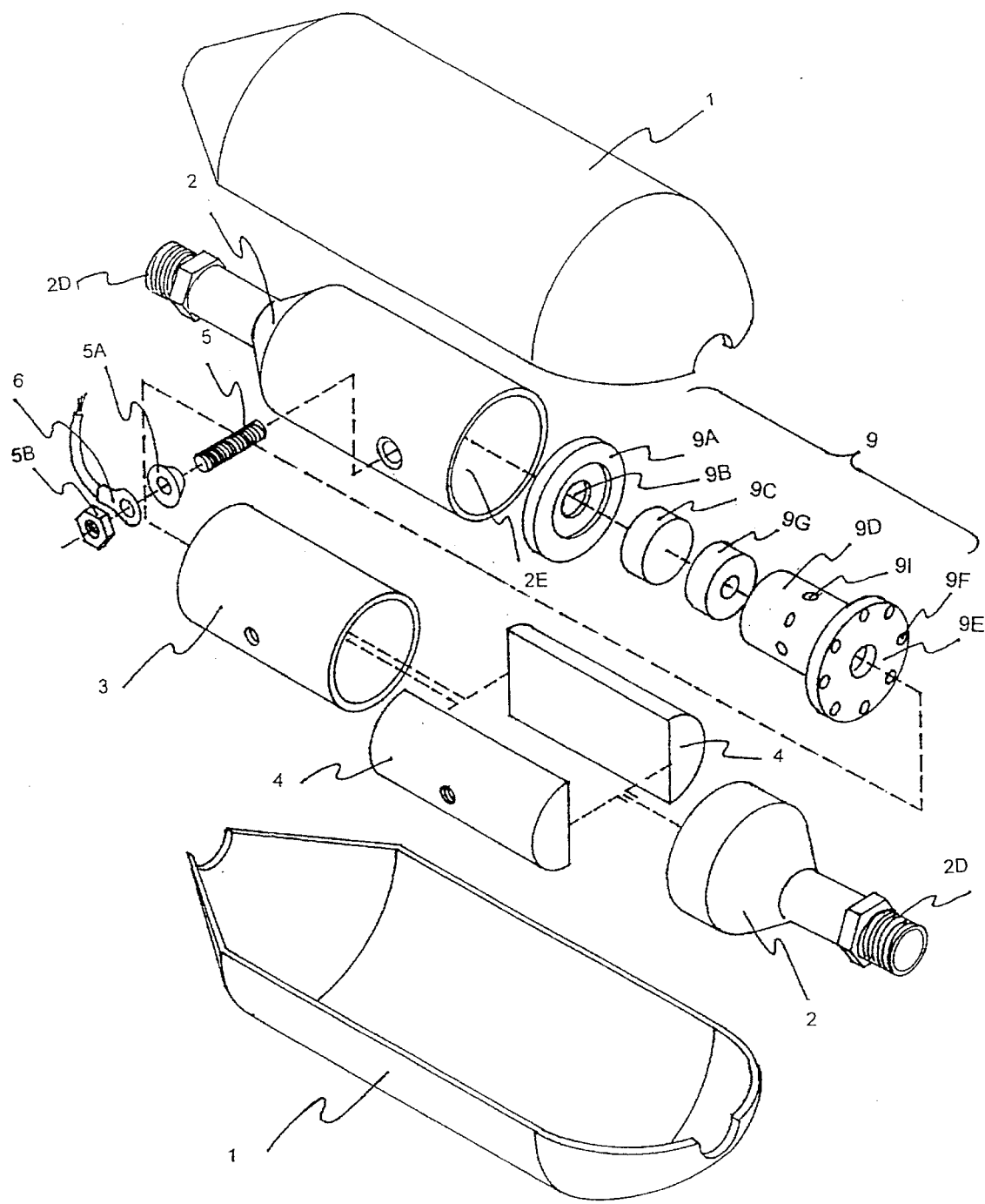
FIG. 3 shows an exploded view of the system's components.
Figure 4:
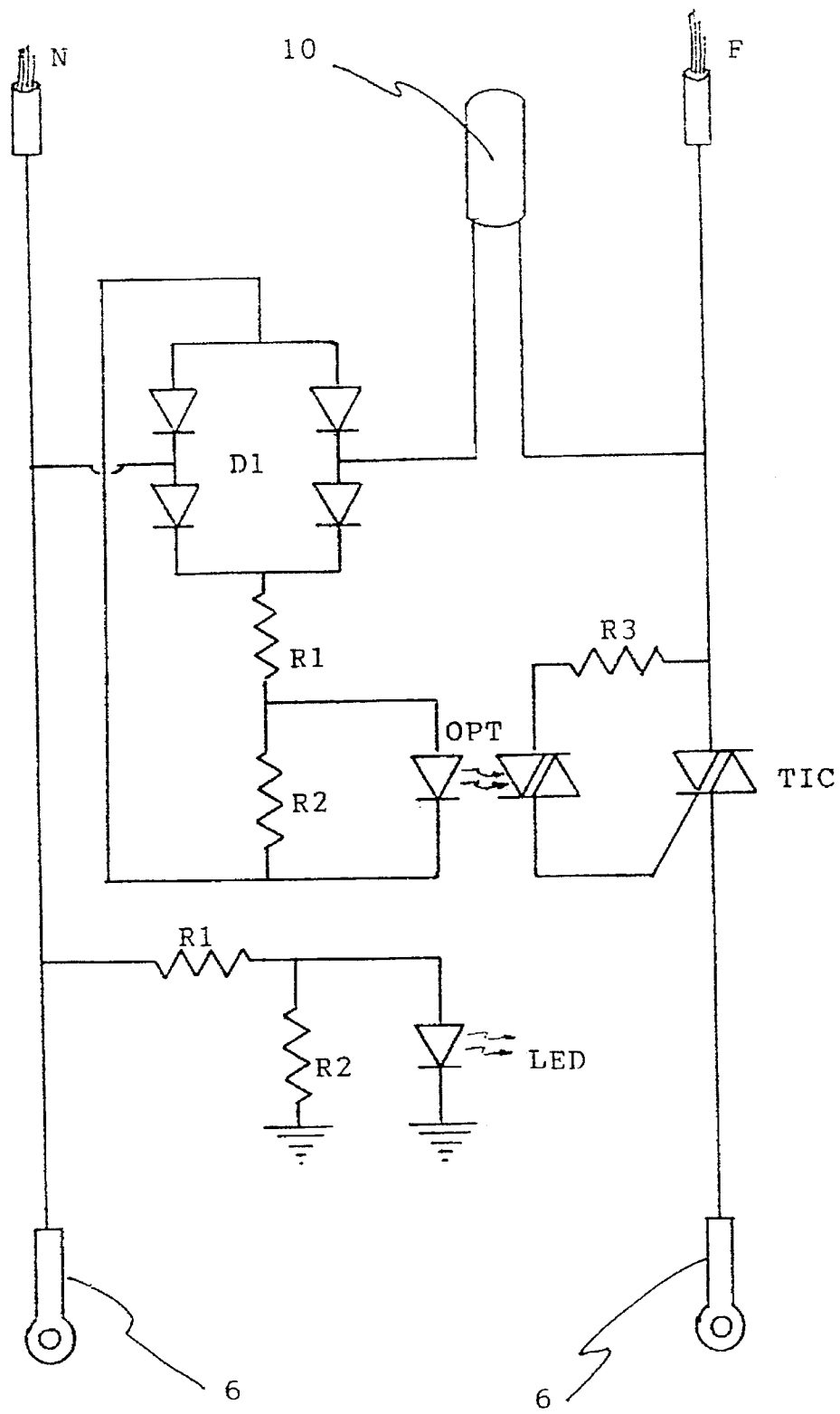
FIG. 4 shows an electric diagram of the system's electronic circuits.

This invention relates to an electropurifying and softening system, of continuous flow, for water and liquids for human, agricultural and industrial consumption, and more specifically, to a system comprising, a plastic protecting cover (1), which contains an electromagnetic circuit for ignition (12), a metallic non ferromagnetic body (2) with an insulating cover (3) graphitized coal electrodes (4) and a magnetic mechanism (9).

The metallic body (2) is provided at each end with a threaded section (2D) by means of which it is possible to couple said metallic body to any piping line in such a way that the liquid may always flow along the interior (2E) of the metallic body (2) with the corresponding flux.

The interior (2E) of the metallic body (2) shelters an insulating material (3) on which electrodes of (4) rest, fastened by means of threaded stems (5) that at the same time serve as terminals, so the terminals of the lines (6) carrying electricity may be connected. Flat surfaces of the graphitized coal electrodes (4) have to be separated from each other in a parallel form, a minimum of 2 millimeters, this way forming the electrical field (7) through which liquid (8) to be treated will flow. By way of this electrocuting field bacteria, virus and pathogenic agents present in the liquid are eliminated; this causes valences of the minerals contained in the water to change, preventing agglutination of minerals to form scale. Thus, soft water is obtained, although molecules of the minerals present from the beginning are still floating in the water.

In order to understand the process, what is achieved is not the elimination of the mineral salts, but the alteration of their valences, so that they lose their general and natural physical characteristics which cause agglutination.

The magnetic device of ignition (9) which is placed in the interior of the metallic body (2) and in the entrance end (2G), which at the same time is formed by a receptor lid (9A), in which body exist one or various entrance holes (9B), a container (9D) for 2 permanent magnets (9C and 9G), and an exit lid (9E), which are provided, as said before, of perforations or notches (9F and 9I) through which fluid (8) passes for its flow.

When the fluid (8) enters the metallic body (2) through the main entrance (2G), the only passing way is the entrance perforation (9B), said fluid (8) penetrates through it and because of its force, it pushes the permanent primary magnet (9C) towards the interior; this permanent magnet is blocking the passage of the liquid (8), by virtue of the position of the magnets (9C and 9G) in repellent form (equal poles reject each other) and said rejection will be only overcome when the fluid (8) force pushes the permanent primary magnet (9C), searching said fluid (8) the perforations (9I and 9F) to enter the field of electrocution (7) between the graphitized coal electrodes (4).

The motion of the permanent primary magnet (9C), when changing its position, activates the magnetic switch (10), same that must be always situated in the exterior of the metallic body (2), near the magnetic field of the permanent primary magnet (9C) in order that said switch (10) is activated by the movement of the primary magnet (9C) and this, at the same time, activates the electronic circuit (12), that will permit the passage of electric current towards the electrodes (4) so that the field of electrocution (7) operates as it should.

What is claimed is:

1. A liquid purifying and softening system comprising in combination:

a protective plastic cover internally containing a liquid flow passageway through a non ferromagnetic metallic body; and a purifying and softening system contained within said metallic body further including
      a pair of graphitized coal electrodes for creating an electric field,
      an electrical system for carrying electricity to said electrodes, and
      a magnetic switching system for energizing said electrical system only in the presence of liquid flow through said metallic body.

2. The system of claim 1 wherein said electrical system includes:

electric circuit means passed through said metallic body and insulated therefrom for passing electrical current to said electrodes to establish said electric field.

3. The system of claim 2 wherein the electrodes comprise flat surfaces separated from each other at a minimum distance of two millimeters, for eliminating bacteria and pathogenic agents in the presence of said electric field.

4. The system of claim 2 whereby said liquid purifying and softening system changes the valences of mineral elements contained in liquids flowing through said metallic body in response to said electrical field.

5. The system of claim 1 wherein said switching system further comprises a permanent magnet inside said metallic body movable in response to liquid flow through said metallic body, and a magnetically responsive switch outside said metallic body actuated by movement of said permanent magnet for establishing said electrical field.

* * * * *